United States Patent [19]

Greidanus et al.

[11] Patent Number: 4,965,128

[45] Date of Patent: Oct. 23, 1990

[54] BIODEGRADABLE POLYMER SUBSTRATES LOADED WITH ACTIVE SUBSTANCE SUITABLE FOR THE CONTROLLED RELEASE OF THE ACTIVE SUBSTANCE BY MEANS OF A MEMBRANE

[75] Inventors: Pieter J. Greidanus, Bergschenhoek; Jan Feijen, Hengelo; Marinus J. D. Eenink, Enschede; Johannes C. Rieke; Jan Olijslager, both of Delft; Jan H. M. Albers, Rijswijk, all of Netherlands

[73] Assignee: Nederlandse Organisatie Voor Toegepast-Natuurwetenschappe Lijk, The Hague, Netherlands

[21] Appl. No.: 168,631

[22] Filed: Feb. 26, 1988

Related U.S. Application Data

[63] Continuation of Ser. No. 745,256, Jun. 14, 1985, abandoned.

[30] Foreign Application Priority Data

Jun. 15, 1984 [NL] Netherlands .................. 8401912

[51] Int. Cl.$^5$ .................. B01D 39/00; D02G 3/00
[52] U.S. Cl. .................. 428/398; 210/500.22; 210/500.23; 428/372; 428/376
[58] Field of Search .................. 428/376, 398, 372; 210/500.23, 500.22

[56] References Cited

U.S. PATENT DOCUMENTS

| | | | |
|---|---|---|---|
| 4,135,514 | 1/1979 | Zaffaroni et al. | 424/427 X |
| 4,214,020 | 7/1980 | Ward et al. | 427/296 |
| 4,231,877 | 11/1980 | Yamauchi et al. | 210/321 B |
| 4,440,853 | 4/1984 | Michaels et al. | 435/68 |
| 4,460,641 | 7/1984 | Barer et al. | 428/398 |
| 4,464,321 | 8/1984 | Pittalis et al. | 428/398 |
| 4,595,583 | 6/1986 | Eckenhoff et al. | 424/438 |

FOREIGN PATENT DOCUMENTS 0061192 9/1982 European Pat. Off. .
0126827 12/1984 European Pat. Off. .

OTHER PUBLICATIONS

S. Sourirajan et al. in "Reverse Osmosis and Synthetic Membranes", Chapter 7, 1977.
Robert E. Kesting in "Reverse Osmosis and Synthetic Membranes", Chapter 5, 1977.
Israel Cabasso et al. in "Polysulfone Hollow Fibers," II. Morphology, Journal of Applied Polymer Science, vol. 21, pp. 165-180, 1977.
Pitt et al. in "Biodegradable Drug Delivery Systems Based On Alphatic Polyesters: Application to Contraceptives and Narcotic Antagonists", Naltrexone. Research Monograph, National Institute on Drug Abuse, vol. 28, 1980, pp. 232-253.
A. Schindler et al. in "Biodegradable Elastomeric Polyesters", Polymer Preprints, 23 (1982) pp. 111-112.
Pitt et al. in "The Design of Controlled Drug Delivery Systems Based on Biodegradable Polymers", vol. 1, MPT Press Ltd., 1980, pp. 17-46.
Chemical Abstracts, vol. 97, No. 22, p. 391 (Nov. 1982).
Chemical Abstracts, vol. 85, No. 2, p. 252 (Jul., 1976).
Chemical Abstracts, vol. 89, No. 4, p. 401 (Jul., 1978).
Polymer News, vol. 8, pp. 230-236 (1982) *Hydrogels and Biodegradable Polymers for the Controlled Delivery of Drugs.*
Journal of Pharmaceutical Sciences, vol. 68, No. 12 (Dec. 1979) *Sustained Drug Delivery Systems II: Factors Affecting Release Rates from Poly(e-caprolactone) and Related Biodegradable Polyesters.*
*Controlled Release Technologies: Methods, Theory, and Applications,* vol. II, Chapter 9, pp. 164-177.

*Primary Examiner*—Lorraine T. Kendell

[57] ABSTRACT

Biodegradable hollow fibres with an asymmetric wall, the cavity of which containing an active substance like a drug, hormone etc. or a dilute form of the latter and both ends of the hollow fibre being closed for the controlled release of the active substance as well as a process for the manufacturing of such hollow fibres.

10 Claims, 1 Drawing Sheet

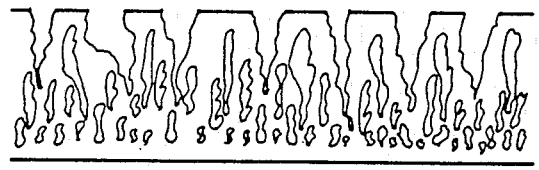

BIODEGRADABLE POLYMER SUBSTRATES LOADED WITH ACTIVE SUBSTANCE SUITABLE FOR THE CONTROLLED RELEASE OF THE ACTIVE SUBSTANCE BY MEANS OF A MEMBRANE

This application is a continuation of application Ser. No. 745,256, filed on 6/14/85, now abandoned.

The invention relates to biodegradable polymer substrates loaded with active substance which are suitable for the controlled release of active substance such as a drug, a hormone and the like.

From "Hydrogels and Biodegradable Polymers for the Controlled Delivery of Drugs" by N. B. Graham and D. A. Wood in Polymer News, 1982, volume 8, pages 230-236 all kinds of release systems based on biodegradable polymer substrates loaded with active substance are known which inter alia can be implanted subcutaneously in humans and animals. Such release systems can, for example, have the form of pellets based on a biodegradable polymer which surrounds the active substance a$ a matrix. Such a release system has, however, the disadvantage that the pellets are not surgically removable or removable with difficulty if it should appear later that the patient does not tolerate the drug. One and the same disadvantage is associated with other release systems mentioned in this article such as microcapsules which have an average size of 10 μm. Apart from the above-mentioned disadvantage the release system based, for example, on pellets has the further disadvantage that if a faster or $lower release of the active substance such as a drug is required a different material has always to be used since the rate of release of the active substance is dependent on the breakdown of the polymer matrix.

Furthermore, in the above-named article by N. B. Graham and D. A. Wood films are reported as a release system. However, such films have the disadvantage that for them to be used subcutaneously, a surgical operation is necessary, which is found to be cumbersome.

Furthermore, in "Sustained Drug Delivery Systems II: Factors Effecting Release Rates from Poly (ε-caprolactone) and Related Biodegradable Polyesters" by Colin G. Pitt et al; in J. Pharm. Sc., vol. 68, no. 12, 1979, pages 1534-1538 films based on homopolymers and copolymers of ε-caprolactone, DL-lactic acid and glycolic acid are described. With regard to the macrocapsules based on poly(ε-caprolactone) described in this article the fact is further brought out in particular that these are prepared by melt extrusion, after which the ends of the hollow tube formed, after filling with the drug, are closed. Of the hollow tubes obtained by means of melt extrusion it is claimed in this article that the external diameter thereof for subcutaneous use in humans and animals can be 2.4 mm max. From the examples given it appears that the external diameter of the hollow tubes has a value between 1.85 and 1.90 mm. However, in view of the size of this external diameter, which is considerably greater than 1.3 mm, for human use these macrocapsules should be implanted subcutaneously by-means of a surgical operation. Such a surgical operation is, however, found to be cumbersome. In addition these macrocapsules have the disadvantage that the rate of release of the drug per unit surface area, which can be adjusted by varying the wall thickness of the hollow tube, can only be altered to a very limited extent, for example by a factor of 2-3.

More especially, with regard to the production technique reported in the last-named literature reference, viz. melt extrusion, the point can be brought out that this technique entails a certain thickness of the membrane, i.e. the wall thickness of the hollow tube to be used for the manufacture of the macrocapsules. In view of the fact that the active substance to be used should be liberated at a certain rate from the macrocapsule provided with a compact wall, the active substance should have both a high solubility in the (co)polymer and also a large diffusion coefficient through the (co)polymer. Since the (co)polymers should in addition also be biodegradable, the choice of the number of suitable (co)polymers to be used for the manufacture of the macrocapsules is very limited and in view of the text of the last-named literature reference, attention being drawn in particular to the passage appearing on page 1534, left-hand column, reading "Release from poly(DL-lactic acid) was very slow when diffusion controlled", is evidently limited to poly(ε-caprolactone). From "Controlled Release Technologies: Methods, Theory and Applications", vol. II by A. F. Kydonieus, page 165 ff, CRC Press Inc. the use of hollow fibres for the release of insect pheromones is known. As, however, specified, such hollow fibres are open at one end so that they are therefore unsuitable for a controlled release of drugs in subcutaneous use in humans and animals.

A search has been made for biodegradable substrates loaded with active substance such as a drug based on polymer compositions which have an easily adjustable rate of release for the active substance by means of a simple change in the release characteristics of the substrate, only degrade after the active substance has been fully released from the substrate, and can contain any desired active substance such as a drug and the like.

In addition, if used subcutaneously, such substrates should be easy to implant subcutaneously by means of injection so that a surgical operation is superfluous and be easily removable if it later appears that the patient does not tolerate the drug.

It was found that the above-named object can be achieved by means of a substrate consisting of a hollow fibre with an asymmetric wall based on a biodegradable (co)polymer and obtained by means of coagulation techniques, the hollow cavity of the hollow fibre containing an active substance or a dilute form of the latter and both ends of the hollow fibre being closed.

More in particular the invention relates to hollow fibres with closed ends filled with an active substance for the controlled release of the active substance, the permeability of the wall of the hollow fibres is adjustable by means of coaguation techniques in such a way that hollow fibres based on one type of material may always have a good permeability for any type of active substance.

The above mentioned term "asymmetric wall" relates to the variation of the porosity across the wall of the hollow fibres according to the invention from high (outer or top layer) to low (inner layer). In view of the above it is stated that the porosity of the wall of the hollow fibres is in fact determined by the porosity of the outer or top layer and that in this respect the wall thickness as such does only play a neglectable part. Such an asymmetric wall is elucidated by FIG. 1, illustrating a cross-section of a wall of a hollow fibre according to the invention.

The following may be mentioned as biodegradable polymer materials to be used for the hollow fibres: polyhydroxy acids like polylactic acid, polyglycolic acid, poly(β-hydroxybutyrate), poly(hydroxyvalerate), poly(ε-caprolactone) and also copolymers derived therefrom as well as poly(α-amino acids) like polyglutamic acid and copolymers derived therefrom.

For subcutaneous use of the substrates according to the invention in humans and animals (co)polymers are preferably used which generate no exogenous products after degradation. Examples of these are polylactic acid, poly(β-hydroxybutyrate), polydepsipeptide, poly(α-amino acids), and also copolymers derived therefrom.

The hollow fibres used according to the invention have an external diameter of 1.3 mm max. when they are used subcutaneously in humans. Because of this external diameter the substrates according to the invention can be injected so that a cumbersome surgical operation can be omitted. Since the substrates according to the invention can have a length even of centimetres, preferably of 1–2 cm, they are easily traceable if the patient does no tolerate the implanted drug. For veterinary use both the external diameter of the hollow fibres and also their length can, of course, be considerably larger, for example an external diameter of approximately 3 mm and a length advantageously of 2–5 cm.

In the hollow cavity of the hollow fibres any desired active substances can be used such as drugs, hormones and related products.

The polymer substrates according to the invention, when implanted, release the active substance to the body over a certain time which can vary, for example, from one week to one year, after which the closed hollow fibre which has acted as a reservoir for the active substance degrades to products which can be excreted from the body. The release period referred to above as well as the rate of release of the active substance used associated with it can be adjusted in a simple manner, according to the invention, by adjusting the production conditions in the manufacture of the hollow fibres.

The biodegradable polymer substrates loaded with active substance according to the invention can, moreover, be used in agriculture and horticulture, insecticides, pheromones, repellants and related products being suitable for use as the active substance. In this use, too, the biodegradable, i.e. capable of being broken down by hydrolysis, polymer substrates according to the invention break down after the active substance has been released to the surroundings. Examples of such polymers which can be broken down by hydrolysis are polyhydroxy acids like polylactic acid, polyglycolic acid, poly(β-hydroxybutyrate), polycaprolactone, and also copolymers derived therefrom as well as poly(α-amino acids) like polyglutamic acid and copolymers derived therefrom.

Further the invention relates to a process for the manufacture of hollow fibres with an asymmetric wall having an adjustable wall permeability for the controlled release of an active substance introduced in such hollow fibres by means of coagulation techniques.

More in particular the hollow fibres can be manufactured by means of the following techniques:
(a) wet spinning or coagulation spinning and
(b) "dry-wet" spinning.

Re (a): In wet spinning or coagulation spinning a polymer solution is fed via a spinning pump to a spinning head in which a spinning plate or spinneret is mounted. In the spinning head the polymer solution is spun through a ring-shaped channel. The inside of this channel consists of a hollow needle through which an injection medium is metered in via a separate feed system. This injection medium can, for example, consist of a coagulant or a coagulant/solvent combination. The spun fibre is introduced directly into a coagulant. In this process the solvent is displaced by the coagulant. The fibre then obtained is no longer fluid or sticky and can be dried and wound. The choice of the solvent or of the coagulant (non-solvent combination) is important because it determines the molecular conformation in the solvent system and the rate of coagulation. This last aspect again has an influence on the porous structure of the fibre wall and consequently on its permeability.

Re (b): The "dry-wet" spinning differs from the wet spinning or coagulation spinning dealt with under a) in that in "dry-wet" spinning the polymer solution which emerges from the spinning head first passes an air slit before it comes into contact with the coagulant. This spinning method has the advantage that the fibre can be stretched in the air slit, which is generally not possible with a coagulated fibre without damaging the fibre wall. By means of this method a larger range of spinning speeds can be achieved. In addition to the fact that the wall thickness and fibre diameter are more readily adjustable with this "dry-wet" spinning method than in the case of wet spinning, this technique also has as an important advantage the fact that the skin formation occurring in the process can better be influenced. Specifically, with this method it is possible to manufacture fibres with a porous wall which are provided with a very thin but adjustable compact skin.

In this respect it is mentioned that in addition to the above indicated spinning parameters the temperature as well as the composition of the polymer solution, of the coagulating medium and of the injection medium, as well as additives introduced into the polymer solution like polyvinylpyrrolidone or lactide, which normally have a porosity-increasing effect determine the permeability of the fibre wall.

The rate of release of the active substance per unit surface area of the wall of the hollow fibre can be substantially altered by means of the spinning techniques mentioned under (a) and (b); if cresyl violet acetate is used as a standard, the release rate can be varied by a factor of approximately 1000. This is considerably more than is possible with the hollow tubes obtained by means of melt extrusion which can only be varied as regards the wall thickness, viz. by a factor of 2–3.

The hollow fibres manufactured in the embodiments below have been manufactured by means of the technique mentioned under (b), viz. "dry-wet" spinning.

To determine the release characteristics of the hollow fibres use is made of cresyl violet acetate (9-amino-5-imino-5H-benzo[α]--phenoxazine-acetic acid salt; molecular weight 321; dyestuff which as regards molecular weight and structure to some extent resembles oestrogen hormones.

The values for the release of cresyl violet acetate reported in the Examples below were determined as follows.

The hollow fibres were cut into lengths of 25 cm and filled with a 2% (w/w) solution of cresyl violet acetate in water. The filled fibres were sealed with silicone rubber glue (Dow Corning) and then placed in glass vessels which were filled with 25 ml of distilled water. The release of the dyestuff was determined spectrophotometrically. The test method was carried out at room temperature, the content of the glass vessels being stirred one to two times per day. The spectrophotometric absorption took place at 650 nm (zero) and 585 nm (peak). After the measurement the samples were again returned to the glass vessels.

The following examples serve to illustrate the invention which, however, is in no way limited thereto.

In the spinning head the internal diameter of the ring-shaped channel was 1.0 mm and the external diameter of the hollow needle present therein was 0.6 mm.

EXAMPLE I

Spinning conditions:

20% w/w solution of poly-lactic acid (MW=450,000) in N-methylpyrrolidone; temperature: 80° C.; rate: 2 ml/min.
Injection fluid: water; flow rate: 40 ml/h
Spinning bath: water; temperature: 20° C.
Spinning speed: 4 m/min.
Spin height: 1, 2 and 8 cm with respect to spinning bath.

Release of cresyl violet acetate from the hollow fibres manufactured with an external diameter of approximately 650 $\mu$m and an internal diameter of approximately 400 $\mu$m

| injection fluid (ml/h) | 40 | 40 | 40 |
|---|---|---|---|
| spin height (cm) | 1 | 2 | 8 |
| release ($\mu$g/cm of fibre/day) | 2 | 10 | 15 |

EXAMPLE II

Spinning conditions

15% w/w solution of poly-lactic acid (MW=125,000) and 5% w/w poly(vinylpyrrolidone) (MW=50,000) in chloroform; temperature: 45° C.; speed: 0.6 ml/min.
injection fluid: ethanol; flow rate: 10 and 20 ml/h
spinning bath: methanol; temperature: 20° C.
spinning speed: 1 m/min.
spin height: 0 and 1 cm with respect to spinning bath.

Release of cresyl violet acetate from the hollow fibres manufactured with an external diameter of approximately 800 $\mu$m and an internal diameter of approximately 600 $\mu$m

| injection fluid (ml/h) | 10 | 20 | 20 |
|---|---|---|---|
| spin height (cm) | 1 | 0 | 1 |
| release ($\mu$g/cm of fibre/day) | 0.1 | 1.1 | 2.3 |

EXAMPLE III

Spinning conditions

15% w/w solution of poly-lactic acid (MW=125,000) and 5% w/w poly(vinylpyrrolidone) (MW=50,000) in chloroform; temperature: 45° C., speed: 0.6 ml/min.
injection fluid: ethanol; flow rate: 20 ml/h
spinning bath: ethanol; temperature: 20° C.
spinning speed: 1 m/min.
spin height: 0.1 and 5 cm with respect to spinning bath.

Post-extraction of the spun hollow fibres in methanol for three days at a temperature of 20° C. to remove poly(vinylpyrrolidone).

Release of cresyl violet acetate from the hollow fibres manufactured with an external diameter of approximately 750 $\mu$m and an internal diameter of approximately 500 $\mu$m

| injection fluid (ml/h) | 20 | 20 | 20 |
|---|---|---|---|
| spin height (cm) | 0 | 1 | 5 |
| release ($\mu$g/cm of fibre/day) | 0.07 | 0.04 | 0.03 |

EXAMPLE IV

Spinning conditions

13% w/w solution of poly-lactic acid (MW=95,000) and 4% w/w lactide in dioxane; temperature: 50° C., speed: 1 ml/min.
injection fluid: water; 20 ml/h
spinning speed: 1 m/min.
spin height: 1 and 10 cm with respect to spinning bath.

Release of cresyl violet acetate from the hollow fibres manufactured with an external diameter of approximately 720 $\mu$m and an internal diameter of approximately 620 $\mu$m

| injection fluid (ml/h) | 20 | 20 |
|---|---|---|
| spin height (cm) | 1 | 10 |
| release ($\mu$g/cm of fibre/day) | 0.05 | 2 |

EXAMPLE V

Spinning conditions

12% w/w solution of $\gamma$-ethyl-L-glutamate-co-$\gamma$-piperonyl-L-glutamate (MW=205,000) in N-methylpyrrolidone; temperature: 45° C.; speed: 1 ml/min.
injection fluid: water/N-methyl-pyrrolidone 1:3 v/v; 20 ml/h
spinning bath: water; temperature: 20° C.
spinning speed: 2 m/min.

Release of cresyl violet acetate from the hollow fibres manufactured with an external diameter of approximately 640 $\mu$m and an internal diameter of approximately 560 $\mu$m

| injection fluid (ml/h) | 20 | 20 |
|---|---|---|
| spin height (cm) | 2 | 5 |
| release ($\mu$g/cm of fibre/day) | 0.04 | 0.08 |

We claim:

1. Biodegradable polymer substrate loaded with an active substance selected from the group consisting of drugs, hormones, insecticides, feromones and repellants for the controlled release of the active substance wherein the substrate consists of a hollow fibre having an asymmetric wall formed from a biodegradable polymer selected from the group consisting of polyhydroxy acids and poly(-amino acids) and copolymers thereof by a coagulation technique, said hollow fibre having two ends and having a hollow cavity therewithin, the hollow cavity of the hollow fibre containing the active substance and the ends of the hollow fibre being closed.

2. Polymer substrate according to claim 1, characterised in that the biodegradable polymer is selected from polylactic acid, polyglycolic acid, poly(β-hydroxybutyrate), poly(hydroxyvalerate), poly(ε-caprolactone) or a copolymer derived therefrom and a polyglutamic acid or a copolymer derived therefrom.

3. Polymer substrate according to claim 2, characterised in that the biodegradable polymer is poly-lactic acid.

4. Polymer substrate according to claim 2, characterised in that the biodegradable polymer is poly-γ-ethyl-L-glutamate-co-γ-piperonyl-L-glutamate.

5. Polymer substrate according to claim 1, characterised in that the external diameter of the hollow fibre is 1.3 mm max. and the length of the hollow fibre is 1–2 cm.

6. Polymer substrate according to claim 1, characterised in that the external diameter of the hollow fibre is 3 mm max. and the length of the hollow fibre is 2–5 cm.

7. Biodegradable polymer substrate for used for the controlled release of an active substance selected from the group consisting of drugs, hormones, insecticides, feromones and repellants introduced therein, wherein the polymer substrate consists of an hollow fibre having an asymmetric wall formed from a biodegradable polymer selected from the group consisting of polyhydroxy acids and poly(-amino acids) and copolymers thereof by a coagulation technique.

8. Polymer substrate according to claim 7, characterised in that the biodegradable polymer is selected from poly-lactic acid, polyglycolic acid, poly(β-hydroxybutyrate), poly(hydroxyvalerate), poly(ε-caprolactone) or a copolymer derived therefrom and a polyglutamic acid or a copolymer derived therefrom.

9. Polymer substrate according to claim 8, characterised in that the biodegradable polymer is polylactic acid.

10. Polymer substrate according to claim 8, characterised in that the biodegradable polymer is poly-γ-ethyl-L-glutamate-co-γ-piperonyl-L-glutamate.

* * * * *

UNITED STATES PATENT AND TRADEMARK OFFICE
CERTIFICATE OF CORRECTION

PATENT NO. : 4,965,128

DATED : October 23, 1990

INVENTOR(S) : Pieter J. Greidanus et al.

It is certified that error appears in the above-identified patent and that said Letters Patent is hereby corrected as shown below:

Col. 4, line 60, after "321;" insert --Sigma) which is a--;
Col. 6, following line 22, insert: --spinning bath: water; temperature: 20°C--;
Col. 6, following line 45, ("spinning speed .."), insert: --spin height: 2 and 5 cm with respect to spinning bath.--;
Col. 6, line 64, "(-amino acids)" should read --(α-amino acids)--;
Col. 7, line 20, "used" should read --use--;
Col. 8, line 6, "(-amino acids)" should read --(α-amino acids)--;

Signed and Sealed this

Fifth Day of May, 1992

Attest:

DOUGLAS B. COMER

Attesting Officer

Acting Commissioner of Patents and Trademarks